US00PP09498P

United States Patent [19]

Magee

[11] Patent Number: Plant 9,498

[45] Date of Patent: Apr. 9, 1996

[54] ILEX HYBRID VARIETY NAMED 'CONIVE'

[75] Inventor: Jack M. Magee, Hwy 25 W. Rte. 1 Box 297, Poplarville, Miss. 39470

[73] Assignees: Jack M. Magee, Poplarville, Miss.; Flowerwood Nsy Inc., Mobile, Ala.

[21] Appl. No.: 413,270

[22] Filed: Mar. 30, 1995

[51] Int. Cl.[6] ..... A01H 5/00

[52] U.S. Cl. ..... Plt./65

[58] Field of Search ..... Plt./65

[56] References Cited

U.S. PATENT DOCUMENTS

P.P. 8,792 6/1994 Fischer ..... PLT./65

P.P. 8,793 6/1994 Fischer ..... PLT./65

*Primary Examiner*—James R. Feyrer

[57] ABSTRACT

A new and distinct variety of Ilex plant found as an openly pollinated seedling of *Ilex Hybrid 'Mary Nell'*. The variety possesses a dense, upright, pyramidal growth habit, flower which produce functional pollen and ovaries, attractive orange-red fruit, glossy dark green foliage, and distinctly arranged leaf serrations.

2 Drawing Sheets

BACKGROUND OF THE INVENTION

This new Ilex variety was found as an openly pollinated seedling of *Ilex Hybrid 'Mary Nell'*, an unpatented variety, maintained in the Evergreen Nursery at Poplarville, Miss. The seedling was found in May, 1989. The new and distinct *Ilex Hybrid* plant of this invention comprises a novel and valuable holly plant with an upright, dense, pyramidal shape, attractive orange-red fruit, and unusual leaf serrations. As with the parent, the plant of this invention may be advantageously employed as a specimem appointment, in either formal or informal groupings, and is very attractive in mass plantings. The plant serves well in foundation plantings and is adapted for culture as a potted plant. This plant is responsive to pruning and training and may be used in forming dense hedges, and maintained without an excessive amount of care.

Asexual propagation of the new plant by cuttings has been under Mr. Magee's direction at the same location. Several generations of the new plant have been evaluated and the distinctive characteristics of the plant have remained stable.

SUMMARY OF THE INVENTION

The following are the most outstanding and distinguishing characteristics of this new cultivar when grown under normal horticultural practices in Poplarville, Miss.

1, Upright, dense and pyramidal in nature.

2, Hardy to Zone 7.

3, Heat and drought tolerant.

4, Fast growth rate under normal fertilization and moisture conditions.

5. Tolerates most soils from moist to dry and from sand to clay.

6. Relatively pest resistant.

7. Very desirable in planters.

8. Makes a good hedge. The short petiole and internode length in addition to the unique arrangement of stiff spines results in a plant which produces an impenetrable thicket.

9. Easy to root from cuttings collected any time of year.

10. Flowers are perfect and can effectively pollinate other forms of Ilex.

11. Produces attractive orange-red fruit in the fall which persist into the winter and may result in bird visitation.

12. Has the ability to be sheared and trimmed to be kept within prescribed limits.

13. Mature leaves are a glossy dark green color with attractive spines.

DESCRIPTION OF THE DRAWINGS

This new *Ilex Hybrid* variety is illustrated by the accompanying photographic prints in which.

Figure 1:
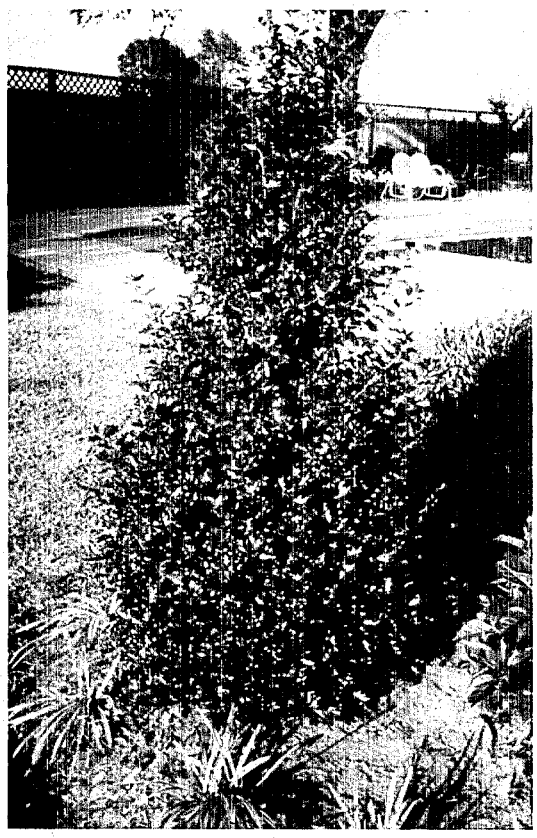
FIG. 1 discloses the dense, upright, pyramidal shape of the new plant.
Figure 2:
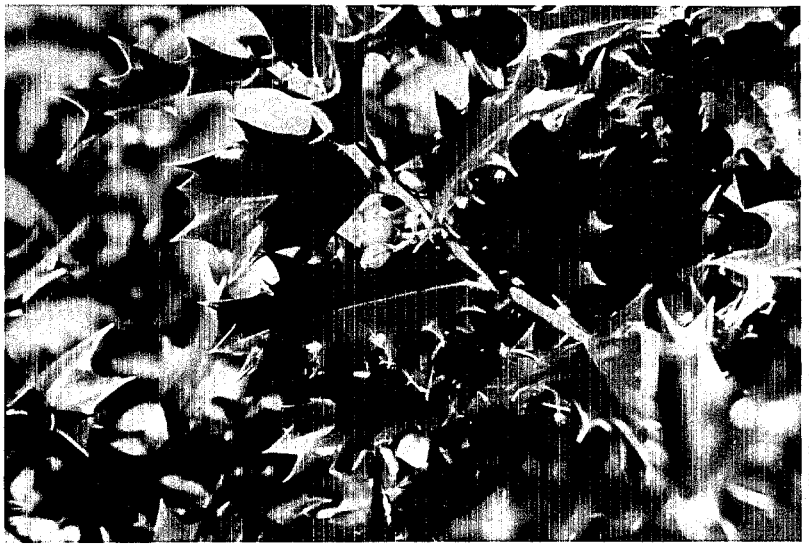
FIG. 2 shows a close-up view of the attractive orange-red fruit and mature foliage of the new variety.
Figure 3:
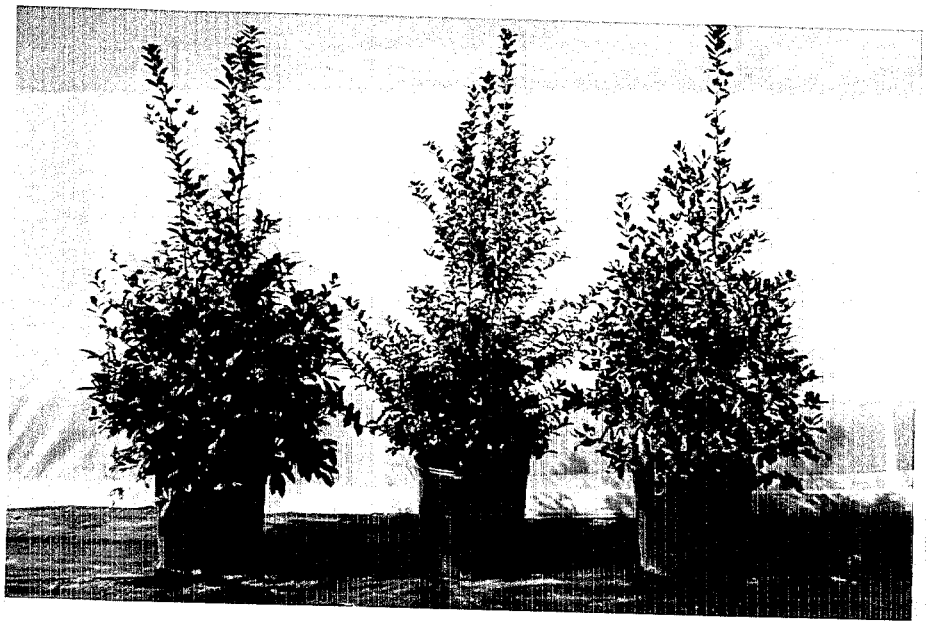
FIG. 3 is a side-by-side photograph of (fromleft to right) the parent plant *Ilex Hybrid 'Mary Nell'*, the new variety, and *Ilex Hybrid 'Nellie R. Stevens'*. The mid-winter photograph shows the new variety's upright, dense, pyramidal shape and dark green mature foliage color.
Figure 4:
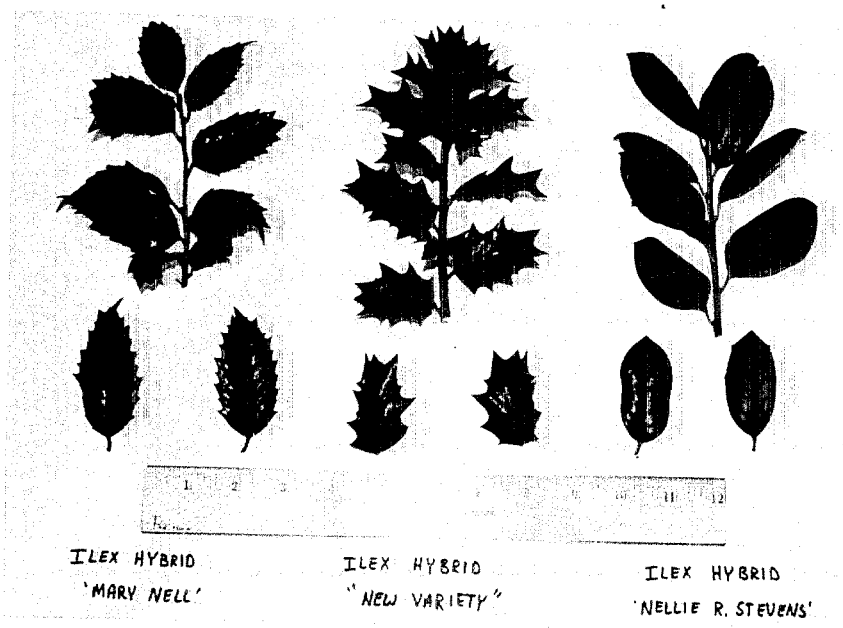
FIG. 4 is also a side-by-side photograph illustrating the leaf shapes and sizes of (from left to right) the parent plant *Ilex Hybrid 'Mary Nell'*, the new variety, and *Ilex Hybrid 'Nellie R. Stevens'*. Also evident is the glossy leaf of the new variety compared to the other hollies.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Ilex based on my observations made of plants grown in wholesale commercial production practices, in greenhouses, and established landscape plantings in Poplarville, Miss.

| Characteristic | Distinctive Characteristics: 'Conive' | 'Mary Nell' | 'Nellie R. Stevens' |
|---|---|---|---|
| Height (Mature) | 15–20' | 15–25' | 15–25' |
| Width (Mature) | 12–15' | 12–15' | 12–15' |
| Leaf Length | 1¾–2¾" | 2⅝–3½" | 2¼–3" |
| Leaf Width | 1¼–1¾" | 1⅛–1¾" | 1–1½" |
| Petiole Length | ⅛–¼" | ¼–½" | ½–⅝" |
| Internode Length | ⅜–¾" | ⅝–1¼" | ⅝–1¼" |
| Leaf glossiness (Mature) | Glossy | Very glossy | Glossy |
| Leaf Shape | Ovate to lanceolate | Ovate to broadly lanceolate | Ovate |
| Leaf Spines (Pairs) | 5–7 | 9–11 | 2–3 |
| Terminal Spines | 3 | 1 | 1–3 |
| Fruit Color | Orange-Red Group 33A | Red Group 40A | Orange-Red Group 33A |
| Flowers Sex | Male & Female | Female only | Female only |
| Leaf Base | Broadly Acute | Obtuse | Obtuse |
| Mature Shape | Dense, Upright Pyramidal | Upright Pyramidal | Upright Pyramidal rounded with age |
| Hardiness | Zone 7 | Zone 7 | Zone 6 |

The parent plant of the new variety 'Conive' is *Ilex 'Mary Nell'* which originated from a controlled cross made in 1962 by Joe McDaniel at Tom Dood Nurseries in Semmes, Ala. The female parent was *Ilex (cornuta* Burfordii'×pernyi) 'Red Delight'.The selection of Henry Hohman, Kingsville Nurseries, Kingsville, Md. The male parent was *Ilex latifolia. Ilex 'Mary Nell'* was named in 1981 by Thomas H. Dodd, Jr. after Joe McDaniel's wife.

*Ilex Hybrid 'Nellie R. Stevens'*, which is very popular in the industry, is a hybrid between *Ilex aquifolium* and *Ilex cornuta.* It was released by G. A. Van-Lennep, Jr., St. Michael, Md. in 1954. It is named for the owner, Nellie R. Steven, Oxford, Md. This non-patented plant is comparable to the new plant, however, there are many differences. The flowers of the new variety contain male and female parts which are both functional compared to the *Ilex 'Nellie R. Stevens'* and *Ilex 'Mary Nell'* flowers which have viable ovaries but the anthers produce no pollen. The new variety also has more spines, 5–7 (pairs) compared to 2–3 (pairs) and the spines are much more prominent than those of *Ilex 'Nellie R. Stevens'. Ilex 'Nellie R. Stevens'* often has 3 terminal spines, whereas the new variety always has 3 terminal spines. The central terminal spine of the new variety tends to be the same plane as the main leaf blade which is characteristic of *Ilex pernyi.* The spines of *Ilex 'Nellie R. Stevens'* normally point downward at an angle to the main leaf blade, characteristic of *Ilex cornuta.*

It is from the openly pollinated seedlings of the *Ilex 'Mary Nell'* plant that I found the new plant. This new variety will be sold under the trademark Festive.

Classification:

*Botanic.—Ilex Hybrid 'Conive'.*

Form: Upright, dense and pyramidal.

Texture: Medium to coarse.

Height: 15–20'.

Width: 12–15'.

Growth habit: Upright, dense and pyramidal. Fast growth rate under normal fertilization and moisture conditions.

Foliage: Alternate, simple, evergreen, ovate to lanceolate, and vary in size from 1¾–2¾" long and 1¼–1¾" wide. The margins are serrate with 5–7 pairs of stiff prominent spines. The spines vary in length and width from 1/16 to 7/16". The apex is acute with 3 large prominent terminal spines of equal size. The central terminal spine is in the same plane as the main leaf blade, however, the first, third, and occasionally the fifth pair of spines point upward. All other spines are in the same plane as the main leaf blade or pointing slightly downward. After the 3 large terminal spines the length of the spines usually alternates between long and short beginning with a pair of short spines. The base of the leaf is obtuse.

The peticle is ¼" long and the internode length is ⅜–¾". Mid-veins and laterals are impressed on the upper leaf surface and the mid-veins are prominent on the underside. The upper surface of the immature leaves are glossy, glabrous, and Yellow-Green Group 144A. The lower surface of the immature leaves are Yellow-Green Group 144A and matte. As the leaves mature the upper surface becomes Green Group 139A and the lower leaf surface becomes Yellow-Green Group 146C. This mature leaf color persists through the winter. The degree of glossiness of the mature leaf is slightly less than that of the parent plant.

In 1992, the date of initial spring growth was Mar. 10, in Poplarville, Miss. After the initial spring flush there was almost continuous growth until fall ending Oct. 22, also in Poplarville, Miss. This growth pattern was identical to the parent plant. When grown in full sun, the internode length of this plant is ⅜–¾" compared to ⅝–1¼" for the parent plant. When grown in light shade the internode length is ¾–1". As would be expected either plant grown in the shade results in a taller less dense plant with larger leaves.

The average length of terminal growth of the initial spring flush is about 12" for a plant in full sun and 14" when grown in shade. After this initial flush we normally trim the plant lightly and the plant then continues to grown about 8" until we trim it a second time in early fall. The fall growth of about 10" then hides the cut limbs. We finish in the fall with a three gallon plant about 34" tall and 20" wide. I have not noticed a difference in vigor between this plant and the parent. *Ilex 'Mary Nell'* plants grown under identical conditions were also 34" tall and 20" wide at the end of the fall.

Although there are many variables involved it should take about 8–10 years for this plnat to reach a mature height of 15–20' tall and width 12–15'. In the landscape little or no pruning is necessary to produce a dense, upright, pyramidal shrub in full sun. In shade, however, some trimming may be needed to produce the same effect.

Stems: The young shoots and petioles are yellow-Green Group 144A, glabrous, and matte. After one or more years the stems are generally Green-Brown Group 199C, glabrous, and rugose. The pith is solid and uniform.

Flowers: Perfect, small, creamy yellow, inconspicuous, slightly fragrant, borne on previous season's growth from Mar. to May. Buds are globular, Yellow-Green Group 144A, and without foliaceous appendages. Flowers are clustered in the leaf axils and are 4-merous. Unbranched pedicels are about ¼" long and Yellow-Green Group 144A. The four ovate petals are arranged regularly, united at the base, and imbricate in bud. The ovary protrudes from the receptacle and is Green Group 143A. There are four stamen with immature anthers White Group 155D. As the anthers mature and pollen is released the color becomes Yellow Group 3C. Blooms are small to medium in size, Yellow Group 2D, ⅜" diameter, and last on the plant in the garden 2–4 days.

Fruit: Drupaceous, globose, ¼–⅜" diameter, born fasciculate with 2–5 fruits on short unbranched pedicels ¼" long. Each fruit contains 4 pyrenes. Matures to Orange-Red Group 33A in mid-Nov. in Poplarville, Ms. and persists into the winter. Normally fruit set is moderate.

Culture: Grown well in a wide range of conditions and tolerates sun to part shade. Grows in nearly any soil type, from moist to very dry and sand to clay. Responds well to mulching and medium applications of fertilizer; prefers ph 5 to 6.5. Little pruning is needed. Can be sheared. Propagated with semi-hardwood cuttings anytime of the year Pest: Non serious.

I claim:

1. A new and unique variety of Ilex plant named *Ilex Hybrid 'Conive'* as herein shown and described, is characterized by its dense, upright, and pyramidal growth habit, perfect flowers which produce an abundance of pollen, glossy mature leaves, distinctly arranged leaf serrations, orange-red fruit, fast growth rate, resistance to pests, and tolerance of heat, drought, and soil type.

* * * * *